United States Patent
Stroebech et al.

(10) Patent No.: US 11,938,052 B2
(45) Date of Patent: Mar. 26, 2024

(54) OSTOMY APPLIANCE WAFER WITH CONTROLLED PEEL FORCE, PERMEABILITY, AND MOISTURE ABSORPTION

(71) Applicant: Coloplast A/S, Humlebaek (DK)

(72) Inventors: Esben Stroebech, Hoersholm (DK); Mads Lykke, Broenshoej (DK); Anders Bach, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 768 days.

(21) Appl. No.: 17/072,059

(22) Filed: Oct. 16, 2020

(65) Prior Publication Data
US 2021/0030582 A1 Feb. 4, 2021

Related U.S. Application Data

(63) Continuation of application No. 15/004,100, filed on Jan. 22, 2016, now Pat. No. 10,842,663, which is a continuation of application No. 13/132,686, filed as application No. PCT/DK2009/050322 on Dec. 7, 2009, now Pat. No. 9,271,863.

(30) Foreign Application Priority Data

Dec. 8, 2008 (DK) .......................... PA 2008 01728

(51) Int. Cl.
 A61F 5/443 (2006.01)
 A61F 5/448 (2006.01)
 A61L 24/04 (2006.01)
 A61L 24/06 (2006.01)
 A61F 5/445 (2006.01)

(52) U.S. Cl.
 CPC .............. *A61F 5/443* (2013.01); *A61F 5/448* (2013.01); *A61L 24/043* (2013.01); *A61L 24/046* (2013.01); *A61L 24/06* (2013.01); *A61F 5/445* (2013.01); *A61L 2400/14* (2013.01)

(58) Field of Classification Search
 CPC ........... A61L 24/00–12; A61L 2400/14; A61F 5/443; A61F 5/448; A61F 5/445
 See application file for complete search history.

(56) References Cited

U.S. PATENT DOCUMENTS

| | | | | |
|---|---|---|---|---|
| 5,545,154 | A * | 8/1996 | Oberholtzer | A61F 5/443 604/336 |
| 6,303,700 | B1 * | 10/2001 | Chen | A61L 24/043 424/448 |
| 6,387,082 | B1 * | 5/2002 | Freeman | A61F 5/448 604/338 |
| 2005/0096611 | A1 * | 5/2005 | Stoyer | A61F 5/443 604/332 |
| 2009/0306571 | A1 * | 12/2009 | Lam | C08L 83/00 524/588 |

* cited by examiner

*Primary Examiner* — Susan S Su
(74) *Attorney, Agent, or Firm* — Coloplast Corp., Coloplast A/S; Nick Baumann

(57) ABSTRACT

An ostomy appliance wafer has a skin facing layer of adhesive applied to a proximal side of a film layer to define a proximal skin facing surface of the ostomy appliance wafer, and the skin facing layer of adhesive has a thickness in a range between 25 to 200 micrometers.

16 Claims, 2 Drawing Sheets

OSTOMY APPLIANCE WAFER WITH CONTROLLED PEEL FORCE, PERMEABILITY, AND MOISTURE ABSORPTION

FIELD OF THE INVENTION

This invention relates to a body waste collecting device comprising a pressure sensitive adhesive construction for attaching a collecting pouch on human skin, said construction contains at least two layers of soft adhesive.

BACKGROUND OF THE INVENTION

When adhering a collecting device to human skin the major situations that need to be considered are the following:
1) Wearing the adhesive; the adhesive should stay in place and not detach or fall off because of skin or body movements.
2) Removing the adhesive; the adhesive should be easy to remove without excessive pain or skin damage as a result.

This is a paradox—the adhesive should stay in place nicely, but should also be easy to remove. The solution today is a compromise in adhesive characteristics that accommodate both situations.

The soft adhesive systems have shown to be advantageous in the use as a skin friendly adhesive wafer.

New opportunities are obtained using a permeable adhesive material to design a skin friendly adhesive wafer. The load of filler in order to handle moisture from the skin is lower thereby increasing the softness of the adhesive. Moisture permeable materials can be formulated to be very soft as a material property. This is the main factor in order to design a soft adhesive system. Furthermore, permeable films can also be formulated with very soft properties and thus the adhesive wafer construction can be designed with a certain softness. As for wearing a soft adhesive wafer on the skin (in contrast to a standard hydrocolloid wafer) a high degree of comfort and security is obtained, as the soft adhesive wafer will be able to follow the body movements without having the feeling that the adhesive will peel off.

The construction described in International Patent Application No. PCT/DK2008/050148 is a two layer adhesive construction of a soft water impermeable, moisture permeable skin facing adhesive that allows the moisture from the skin to diffuse through the adhesive material. The construction further comprises a non skin facing layer that is water impermeable, moisture permeable containing absorbing particles allowing the moisture to be absorbed in the particles.

There has now surprisingly been found a way to isolate the two situations mentioned above, such that the ability of the soft adhesive to be easily removed can be controlled independently of the ability of the soft adhesive to stay in place.

SUMMARY OF THE INVENTION

The invention relates to a body waste collecting device comprising a pressure sensitive adhesive construction for attaching a collecting pouch on human skin, the construction contains at least two layers of soft adhesive and a film layer. It has now surprisingly been found that by introducing a layer of film in between the two layers of soft adhesives the peel force can be controlled in an easy and independent way.

BRIEF DESCRIPTION OF THE DRAWING

The invention is disclosed more in detail with reference to the drawings in which.

DETAILED DESCRIPTION OF THE PRESENT INVENTION

Figure 1:
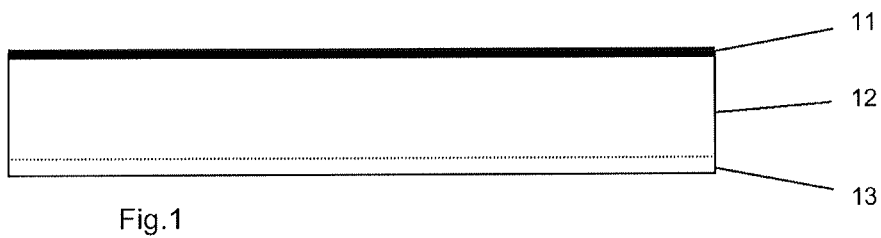
FIGS. 1-2 illustrate the cross section of the construction of a known layered adhesive construction and a construction of an embodiment according to the invention.

The aim of the invention is to adjust the peel force and thereby increase the user's comfort when removing the adhesive, without at the same time decreasing the ability of an adhesive for fastening a collecting device to human skin.

In an embodiment of the invention, a body waste collecting device comprising
a collecting pouch
an adhesive wafer for attachment to the body, comprising
a backing layer
at least one intermediate layer of adhesive
a skin facing layer of adhesive
a film layer,
wherein the intermediate layer of adhesive and the skin facing layer of adhesive comprise liquid impermeable, moisture permeable soft adhesives and the film layer is positioned between the skin facing layer of adhesive and the intermediate layer of adhesive.

By body waste collecting device is meant a device being able to collect and hold the output in a collecting item for a predefined time. The holding in place of the device may be obtained by a skin adhesive and the collection may be obtained by a bag.

In the theory of adhesion, the peel force will decrease with the reduction of the adhesive thickness.

"In adhesive bonds involving peeling of a flexible elastic adhesive from a rigid substrate, the varying of adhesive thickness is shown theoretically to predict a proportional increase of peel force with adhesive thickness". [Theory and Analysis of Peel Adhesion: Adhesive Thickness Effects, D. H. Kaelble, The Journal of Adhesion, vol 37, 1992.]

Thus, in adhesive systems it is possible to control the peel force by changing the adhesive thickness. In order to see a predominant decrease in peel with a reduced thickness of the adhesive, the system has to be soft. A stiff and rigid layer of adhesive will still be a stiff and rigid system after adjusting the thickness of the adhesive. Therefore, such a rigid system may not show the same effect as a system based on soft adhesive.

The adhesive of the wafer needs to be soft in order for the total wafer to be able to stretch. By soft adhesive layer is therefore meant a layer of adhesive with a complex modulus G* as defined herein of less than 50 kPa measured at 32° C. and 1 hz.

The peel force of the soft adhesive of the wafer can be controlled by changing the adhesive thickness. However, the thickness of the adhesive cannot be changed without affecting other functionalities of the wafer. For example if the thickness is too thin the adhesive construction cannot maintain the absorbent characteristics or may not be able to stick to the skin.

In a design with a backing layer and a thin adhesive layer one can obtain the desired effect of lowering the peel force as well. However, such construction can be a challenge while handling the adhesive wafer during application and removal. Such a soft and thin construction will be almost impossible to apply properly to a substrate (skin). Another issue is the moisture handling in order not to damage the skin due to maceration from perspired moisture. This issue will be crucial when the adhesive wafer is attached to a bag like in an ostomy product. As the humidity in the bag will be close to 100%, the skin cannot breathe through the thin adhesive construction and maceration of the skin will eventually occur. Thus, a moisture handling layer is crucial.

It has now surprisingly been found that the peel force of a soft ostomy adhesive wafer can be controlled by adding a film layer in the wafer and still fulfill the requirements of permeability and absorption, thereby having a skin friendly adhesive system.

In order to be able to control the peel force of the skin facing adhesive, the present invention introduces a soft moisture permeable film layer in between the skin facing layer of adhesive and the intermediate layer of adhesive. In this way the adhesive wafer is divided into two separate layers where the thickness of the skin facing adhesive layer can be used to control the peel force and yet allow the moisture to penetrate through the moisture permeable film layer into the intermediate adhesive layer, thereby maintaining a skin friendly adhesive wafer.

In this way the peel properties can be changed without significantly changing other adhesion properties as for example initial tack, shear, and permeability. If changing the recipe one will always compromise other adhesion properties.

The control of the peel force is important in order to tailor the adhesive for special use for example wear time, type of use etc.

By incorporating the film layer for controlling the peel force, a less "lively" adhesive wafer is obtained without significantly compromising the total softness of the system. This is due to the difference in bending radii of the films incorporated in adhesive wafer. By less lively is meant that the adhesive wafer itself will not tend to bend or curl when the protective cover or release liner is removed. This less lively feature is useful when applying the adhesive wafer to the skin resulting in an ease of handling. When introducing a film layer in between the adhesive systems it is also seen that less stretching of the wafer is needed in order to remove the product. It is important for the user to have a soft adhesive wafer that will not stretch too much during removal.

In an embodiment of the invention, the film layer is permeable.

The film layer according to the invention has to be permeable in order for the perspired moisture from the skin to be removed and thus obtain a healthy environment on the skin. In order for the skin to stay healthy a permeability of the film layer has to be above 500 g/m$^2$/24 h, preferably above 1000 g/m$^2$/24 h.

The permeability of the film layer can be a material property or an induced property by e.g. perforating the film layer.

In another embodiment of the invention, the film layer may be perforated.

Perforation of the film layer allows choosing films from the group of non permeable ones. The perforation will make the film layer open. Perforation of a film layer is usually done by making a long line or area of holes or cuts in the film layer. The perforated film layer has to fulfill the permeability criteria as mentioned above.

By a film layer in this context is also meant a non-woven or a foamed film layer. Non-wovens can be produced to have high permeability rates and will thus be suitable for the purpose according to the invention. Foamed film layers can either be produced by open celled foams and thus be highly permeable or be formulated from highly permeable materials. Due to the foaming, a high permeability of the foamed film layer can be obtained even with low permeability material characteristics as the total material thickness of the foamed film layer is low.

According to one embodiment of the invention, the film layer has a higher modulus than the intermediate layer of adhesive. In a preferred embodiment, the film layer has a modulus more than 10 times higher than the modulus of the intermediate layer of adhesive.

In one embodiment of the invention, the thickness of the film layer is below 100 μm. Preferably, the thickness of the film layer is 10-50 μm.

In an embodiment of the invention, the film layer comprises EVA, EBA, PU or PE.

By EVA, EBA, PU or PE is meant EVA (ethylene vinyle acetate), EBA (ethylene butyl acetate), EMA (ethylene methyl acetate), PU (polyurethane) or PE (polyethylene).

In the case of soft adhesive systems the materials used are permeable for moisture. This material feature is used to transport the moisture away from the skin, thereby ensuring a healthy environment and an intact non macerated skin.

Liquid impermeable, moisture permeable layer is a layer that does not allow liquid to penetrate through the layer, but allows moisture to permeate through the layer. This layer is meant to retain perspiration in its liquid state close to the sweat glands, but allows it to slowly diffuse through the layer.

In one embodiment of the invention, the water vapour permeability of the skin facing layer and/or of the intermediate layer of adhesive of the liquid impermeable, moisture permeable adhesive composition is higher than 100 g/m$^2$/24 h, preferably higher than 200 g/m$^2$/24 hrs.

According to an embodiment of the invention, the thickness of the skin facing layer of adhesive is below 200 μm.

According to one embodiment of the invention, the skin facing layer of adhesive is at least 25 μm thick, preferably more than 50 μm thick.

In a preferred embodiment of the invention, the thickness of the skin facing layer of adhesive may be 80-120 μm.

In one embodiment of the invention, the skin facing layer of adhesive is low-absorbent.

By low-absorbent is meant that the water absorption capacity is less than 8%, preferably less than 4%, as defined herein.

Pressure sensitive adhesives for the thin skin facing layer could be any hydrophobic adhesives with good vapour permeability. Such adhesives are typically adhesives that contain one or more polymers to give the adhesive cohesive strength and optionally oils and tackifier to adjust the adhesive properties.

According to one embodiment of the invention, the skin facing layer of the liquid impermeable, moisture permeable adhesive composition comprising a permeable polymer selected from the group of but not limited to polypropyleneoxide, polyurethane, ethylene vinyl acetate, silicone, polyacrylate, and mixtures thereof.

As used herein a moisture permeable polymer means a polymer that has a moisture vapour transmission rate greater than 100 g/m$^2$/24 hrs, preferably greater than 300 g/m$^2$/24 hrs, when measured on a 150 μm film of the material using the method described herein.

According to an embodiment of the invention, the permeable polymer is low-absorbent and absorbs less than 8% in wt, preferably less than 4%, at equilibrium.

In one embodiment of the invention, the skin facing pressure sensitive adhesive is crosslinked.

As used herein a crosslink means a small region in a macromolecule (polymer chain structure) from which more than 2 chains emanate. The linking may be covalent, physical or ionic.

In another embodiment of the invention, the skin facing pressure sensitive adhesive comprises a block copolymer.

As used herein a block copolymer means a copolymer in which the repeating units in the main chain occur in blocks, eg, -(a)m-(b)n-(a)p-(b)q-, where a and b represent the repeating units and m, n, p, q, are numbers.

In a preferred embodiment of the invention, the skin facing pressure sensitive adhesive comprises polypropyleneoxide.

In a preferred embodiment of the invention, the skin facing pressure sensitive adhesive comprises polyurethane.

In a preferred embodiment of the invention, the skin facing pressure sensitive adhesive comprises ethylene vinyl acetate.

The adhesive composition comprising ethylene vinyl acetate may suitably be an adhesive known in the art such as the adhesive composition disclosed, for example in International Patent Application PCT/DK2008/050146.

In a preferred embodiment of the invention, the skin facing pressure sensitive adhesive comprises silicone.

In a preferred embodiment of the invention, the skin facing pressure sensitive adhesive comprises polyacrylate.

According to an embodiment of the invention, the skin facing layer of the liquid impermeable, moisture permeable adhesive composition covers the entire skin facing surface of the adhesive wafer.

According to another embodiment of the invention, the skin facing layer of the liquid impermeable, moisture permeable adhesive composition partly covers the skin facing surface of the adhesive wafer.

In a preferred embodiment of the invention, the skin facing layer of the liquid impermeable, moisture permeable adhesive composition covers at least 75% of the skin facing surface of the adhesive wafer.

According to an embodiment of the invention, the intermediate layer of adhesive is absorbent.

In a preferred embodiment of the invention, the intermediate layer has a water absorption capacity of more than 15%, as defined herein.

It may be advantageous that the intermediate layer of adhesive comprises absorbent particles. According to an embodiment of the invention, the intermediate layer of adhesive comprises absorbent particles.

The particles may be absorbent particles such as salts, hydrocolloids, microcolloids or super absorbers in order for the layer to absorb moisture from skin.

Preferred particle size of the absorbent particles is smaller particles, as they are more difficult to see by the naked eye and will give products that are more pleasing to the eye. An upper limit on particle size is the size of the smallest dimension of the layer. Thus, a 300 µm thick layer should not contain particles with diameters above 300 µm. There is a tendency of the hygroscopic particles to agglomerate and this effect will increase with decreasing particle size. Therefore, a preferred particle size would be from 10-300 µm. Also, the particles may contain an anti agglomerating agent to reduce agglomeration of small particles.

Microcolloid particles are well known in the art e.g. from International Patent Application No. WO 02/066087, which discloses adhesive compositions comprising microcolloid particles. The microcolloid particles may have a particle size of less than 20 microns.

The intermediate layer of adhesive may comprise 1-40% w/w of hydrocolloid (HC) or super absorbent particles (SAP), more preferred 5-30% w/w particles.

Salt may be advantageous to use as absorber in the device of this invention. A salt like sodium chloride has an equilibrium vapour pressure of about 75% RH at skin temperature and will absorb water from skin and output because of the difference in vapour pressure.

In an embodiment of the invention, the intermediate layer of adhesive comprises particles of mineral salt. The salt may be present in an amount of 1-50% w/w, more preferred in an amount of 5-25%.

The salt can be an inorganic salt or an organic salt.

According to one embodiment of the invention, the intermediate layer of adhesive comprises water soluble inorganic salt from the group of but not limited to NaCl, $CaCl_2$, $K_2SO_4$, $NaHCO_3$, $Na_2CO_3$, KCl, NaBr, NaI, KI, $NH_4Cl$, $AlCl_3$ and mixtures thereof, preferably NaCl.

According to another embodiment of the invention, the intermediate layer of adhesive comprises water soluble organic salt from the group of but not limited to $CH_3COONa$, $CH_3COOK$, HCOONa, HCOOK and mixtures thereof.

According to one embodiment of the invention, the intermediate layer of adhesive of the liquid impermeable, moisture permeable adhesive composition comprising a permeable polymer selected from the group of polyalkyleneoxide, polyurethane, ethylene vinyl acetate, silicone, polyacrylate, and mixtures thereof.

Preferably, the skin facing adhesive and the hydrophobic matrix of the intermediate layer of adhesive are identical or close to identical in composition to prevent migration of species between the two layers.

According to an embodiment of the invention, the intermediate layer is based on the same type of polymer ingredients as the permeable adhesive composition used in the skin facing layer. In this way the ingredients of the intermediate layer of adhesive may be selected from the group of but not limited to polypropyleneoxide, polyurethane, ethylene vinyl acetate, silicone, polyacrylate and mixtures thereof, optionally made absorbing by adding particles.

According to one embodiment of the invention, the skin facing layer and the intermediate layer of adhesive have a modulus G* less than 50,000 Pa, preferably less than 20,000 Pa measured at 1 hz and 32° C.

According to an embodiment of the invention, the intermediate layer of adhesive is thicker than the skin facing layer of adhesive.

According to another embodiment of the invention, the skin facing layer of adhesive is less than 33% of the thickness of the intermediate layer of adhesive.

The backing layer of the device of the present invention is preferably in the form of a polymer film, coating, laminate, textile or non-woven. The backing layer is preferably a highly flexible film, being strong enough for attachment of e.g. couplings and/or pouch and for removing the device in one piece, but soft enough to follow the movements of the body.

In one embodiment, the backing layer is a polyurethane film optionally a laminate or a coextruded film or a cast film.

Preferably, the backing layer has thermoplastic elements that enable welding of e.g. a pouch or coupling ring to the adhesive wafer. Preferred thickness of the backing layer is between 15-60 µm in order to maintain the softness of the adhesive wafer.

In one embodiment of the invention, the backing layer is non-vapour permeable.

According to another embodiment, the backing layer is a multi layer film. Each layer in the film gives special properties to the backing layer. A thin weldable layer ensures good joining to the bag or coupling and a thicker soft layer ensures the mechanical properties.

According to another embodiment, the backing layer is a foam where the thickness is between 15 and 500 µm. A suitable foam backing layer is e.g. a polyethylene foam, an ethylenvinyle acetate foam, a polyurethane foam, a polyalkylene oxide and/or polyakylene oxide siloxane foam.

A wafer, according to the invention, is optionally covered in part or fully by one or more release liners, or cover films to be removed before or during application. A protective cover or release liner may for instance be siliconised paper. It does not need to have the same contour as the wafer. The release liner may be of any material known to be useful as a release liner for medical devices.

According to an embodiment of the invention, the collecting pouch is detachable.

According to another embodiment of the invention, the collecting pouch is integrated with the wafer.

The collecting pouch may be detachable from the adhesive wafer by a coupling system or the pouch and the wafer may be integrated with the wafer, e.g. by welding. The two versions are known as one piece or two-piece appliances for ostomy.

By the skin facing surface of the adhesive is meant the side adhering to the skin.

By the pouch facing surface or non skin facing surface is meant the side of the adhesive or backing pointing away from the skin (non bonding side).

According to an embodiment of the invention, the collecting device is an ostomy appliance.

According to another embodiment of the invention, the collecting device is a faecal collecting device.

According to another embodiment of the invention, the collecting device is a fistula collecting device.

DESCRIPTION OF THE PREFERRED EMBODIMENTS

Figure 2:
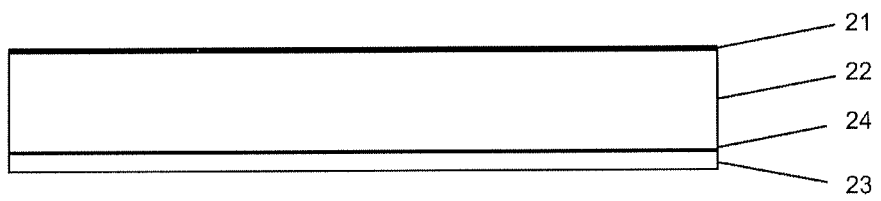
Figure 3:
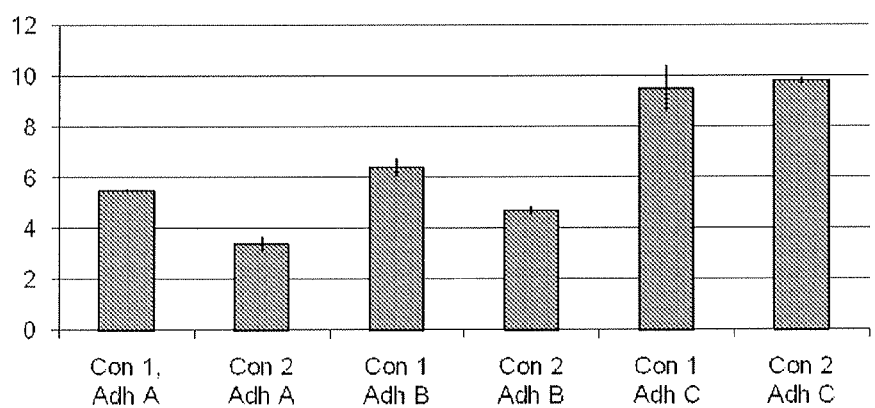
FIG. 3 shows a diagram illustrating the peel force in different adhesive constructions and adhesive compositions.

The invention is now explained more in detail with reference to the drawings of FIGS. 1 to 3 showing preferred embodiments of the invention.

FIG. 1 illustrates a side view of the construction 1 of a known layered adhesive construction containing a backing layer (11), an intermediate layer of adhesive (12) and a skin facing layer of adhesive (13). No film is separating the two layers of adhesive.

FIG. 2 illustrates a side view of the construction 2 of an embodiment according to the invention containing a backing layer (21), an intermediate layer of adhesive (22), a skin facing layer of adhesive (23) and a film layer (24).

FIG. 3 shows a diagram illustrating the peel force in different adhesive constructions and adhesive compositions.

MATERIALS AND METHODS

Methods
Determination of Water Absorption

In order to get better correlation between measured water absorption and actual performance in a humanlike environment, a modified version of the ISO 62 standard was used: Pieces of adhesive of 1×25×25 mm$^3$ were fastened on a piece of glass using double sided adhesive and the constructs were immersed in saline water (0.9% NaCl in demineralised water) at 32° C. After 24 hours the samples were removed and carefully dripped dry and weighed. The change in weight was recorded and reported as weight gain in percent of the original dry weight of the adhesive. In the following we call this value $w_{24h}$ Determination of Moisture Vapour Transmission Rate (MVTR)

MVTR was measured in grams per square meter (g/m$^2$) over a 24 hours period using an inverted Paddington cup method (British Pharmacopoeia, 1993, Addendum 1996, page 1943. HMSO London): A container or cup being water and water vapour impermeable having an opening was used. 20 ml saline water (0.9% NaCl in demineralised water) was placed in the container and the opening was sealed with the test adhesive film. The container, with a duplicate, was placed into an electrically heated humidity cabinet and the container or cup was placed up side down in a way that the water was in contact with the adhesive. The cabinet was maintained at 37° C. and 15% relative humidity (RH). After about an hour, the containers were considered to be in equilibrium with the surroundings and were weighed. 24 h after the first weighing, the containers were weighed again. The weight difference was due to evaporation of vapour transmitted through the adhesive film. This difference was used to calculate Moisture vapour transmission rate or MVTR. MVTR was calculated as the weight loss after 24 h divided by the area of the opening in the cup (g/m$^2$/24 h). If the adhesive film could not support the weight of the water, a supporting film with very high permeability was used as support.

Determination of G*

The parameter G* or complex modulus as defined in "Dynamics of polymeric liquids", Vol. 1, sec. ed. 1987, Bird, Armstrong and Hassager, John Wiley and Sons inc., was used as a measure of the hardness of an adhesive. To avoid any confusion, note that G* in here means the absolute value of the complex G*. G* at 32° C. and 1 Hz was measured as follows: A plate of un-foamed adhesive material was pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurement was carried out at 32° C.

EXAMPLE 1

In example 1 the decrease in peel force was measured in different adhesive systems with and without the film layer.

25×100 mm adhesive strips for peel test were produced in 1 mm thickness. In Table 1 below the adhesive construction is seen. The intermediate adhesive layer formulation and the skin facing layer formulation in a construction were the same.

TABLE 1

| Cons. | Soft adhesive A | | Soft adhesive B | | Standard adhesive C | |
|---|---|---|---|---|---|---|
| 1 | Backing layer | 40 my | Backing layer | 40 my | Backing layer | 40 my |
|  | Intermediate adh. layer | 760 my | Intermediate adh. layer | 760 my | Intermediate adh. layer | 760 my |
|  | Film layer | none | Film layer | none | Film layer | none |
|  | Skin facing adh. layer | 200 my | Skin facing adh. layer | 200 my | Skin facing adh. layer | 200 my |
| 2 | Backing layer | 25 my | Backing layer | 25 my | Backing layer | 25 my |
|  | Intermediate adh. layer | 760 my | Intermediate adh. layer | 760 my | Intermediate adh. layer | 760 my |
|  | Film layer | 15 my | Film layer | 15 my | Film layer | 15 my |
|  | Skin facing adh. layer | 200 my | Skin facing adh. layer | 200 my | Skin facing adh. layer | 200 my |

By 1 my is meant 1 µm. The data in Table 1 indicate the thickness of the layer.

For each adhesive system two constructions were made.

Construction 1 was a 1 mm thick wafer with a 40 µm soft polyurethane top film (Bioflex 180 from Scapa Medical). The intermediate adhesive layer and the skin facing adhesive layer were simply adhered together in a way that they acted as one 960 µm thick adhesive.

Construction 2 was a 1 mm thick wafer with a 25 µm soft polyurethane backing layer (Bioflex 180 from Scapa Medical) and a 15 µm soft polyurethane film layer (Bioflex 180 from Scapa Medical) that divided the adhesive in two. The skin facing adhesive layer was 200 µm and the intermediate adhesive layer was 760 µm.

In construction 1 and 2 the total thickness of the film layer(s) was 40 µm (40 or 25+15 µm).

Three types of adhesives were tested. The intermediate adhesive layer and the skin facing adhesive layer were the same in the respective construction.

By % is meant % (w/w).

A—Soft adhesive system based on

TABLE 2

|  | Soft adhesive system A % |
|---|---|
| PPO ACS003, Kaneka | 96.9 |
| Crosslinker, CR600, Kaneka | 3.0 |
| Catalyst, Pt-VTSC | 0.09 |

The materials were mixed manually in a cup for 1 minute and cured 30 minutes at 90° C. in a mould giving the desired construction. 25×100 mm adhesive strips for peel test were cut out from the wafer. The desired film(s) were chosen for construction 1 and 2.

B—Soft adhesive system based on

TABLE 3

| Trade name (Chemical name) | Name of Supplier | Soft adhesive system B % |
|---|---|---|
| Levamelt 700, 22.5 KGy | Lanxess | 20 |
| Levamelt 500, 16.6 KGy | Lanxess | 11 |
| Levamelt 700 | Lanxess | 6 |
| Oppanol B12 | BASF | 8 |
| Poly Glycol B01/120 | Clarient | 47 |
| Kristalex 100 | Eastman | 8 |
| BHT (2,6-di-tert.-butyl-4-metylfenol) | Sigma | 0.3 |

The adhesives were produced by Z-blade mixing the materials at 120° C. for 1 hour. The gamma radiated materials had to be mixed first with the glycol in order to plasticise the system. Construction of 1 and 2 were made in a heat press similar to the procedure for adhesive C.

C—Standard hydrocolloid adhesive system (25% Kraton D-1161, 35% Arkon P90 resin, 5% dioctyl adipate plasticiser and 35% Blanose 9H4X, Aqualon hydrocolloid) was used as the reference adhesive.

Construction 1 was obtained as the following: All raw materials were blended in a Z-blade mixer equipment at 140° C. for 1 hour. The wafer of a 1 mm thick plate was produced by heat pressing at 90° C. for 10 seconds in a 1 mm deep mould (1×150×150 mm).

Construction 2 was produced by heat pressing the adhesive composition into 200 µm and 760 µm respectively in between two siliconised films. The pressing between two siliconised films makes it possible to remove the siliconised film without destroying the adhesive. Suitable siliconised film is a 110 my PP liner with silicone coating 1808 from Huhtamaki. The desired construction with the 25 µm backing layer and the 15 µm film layer is obtained by laminating the materials by heat pressing in 10 seconds at 90° C. in a 1 mm deep mould. Both constructions were covered with a siliconised protective film prior to heat pressing. The construction is then cut into 25×100 mm strips ready for testing.

The peel measurements were performed on an Instron 5564 with a 100 N load cell at 100 m/min., 25° C. Peel substrate was paper for the soft adhesive constructions and steel for the hydrocolloid adhesive. The paper was fixated to a solid surface with double layered adhesive tape. As a paper peel substrate newspaper is used. Three samples were tested for each construction.

Results

FIG. 3 shows a diagram illustrating the peel force in different adhesive constructions and adhesive compositions. The peel force was measured as AVG Peel Load [N].

A significant peel drop in soft adhesive A and B, going from a peel front of 1,000 µm to 200 µm was seen. A reduction in peel force was obtained without compromising other adhesive properties such as shear, water handling and initial tack. The typical way to reduce the peel force is to reformulate the adhesive in a way that it is easy to remove. When using the stiffer adhesive C, no change in peel force is seen, when adding a film layer, as the stiffer adhesive rather than the film layer tend to control the peel force. In that case the presence of a film layer close to the skin does not affect the peel force.

Reduced extension of the adhesive construction 2 was seen in case of the soft adhesive systems using adhesive A or adhesive B. This was due to the lowering of the peel force. No reduction in extension was seen in adhesive C as the peel force was not reduced.

When lowering the peel force of the adhesive shown in the example, less stretch is also obtained for the adhesive during removal of the adhesive from the substrate. This effect is beneficial for the handling issues as it is desirable to remove the adhesive without an excessive stretch, but yet

What is claimed is:

1. An ostomy appliance wafer comprising:
   a backing layer having a distal side that defines a distal wafer surface of the ostomy appliance wafer, where the distal wafer surface is configured to receive a waste collection pouch;
   a first layer of adhesive applied to a proximal side of the backing layer;
   a film layer applied to the first layer of adhesive; and
   a skin facing layer of adhesive applied to a proximal side of the film layer and defining a proximal skin facing surface of the ostomy appliance wafer;
   wherein the skin facing layer of adhesive has a thickness in a range between 25 to 200 micrometers;
   wherein the skin facing layer of adhesive has a moisture permeability above 100 g/m²/24 h.

2. The ostomy appliance wafer of claim 1, wherein the backing layer and the film layer are formed of the same material.

3. The ostomy appliance wafer of claim 1, wherein the film layer is moisture permeable.

4. The ostomy appliance wafer of claim 1, wherein the film layer has a moisture permeability above 1000 g/m²/24 h.

5. The ostomy appliance wafer of claim 1, wherein the film layer is liquid impermeable.

6. The ostomy appliance wafer of claim 1, wherein the film layer is one of a non-woven layer and a foamed film layer.

7. The ostomy appliance wafer of claim 1, wherein a thickness of the film layer is in a range between 10 to 50 micrometers.

8. The ostomy appliance wafer of claim 1, wherein the skin facing layer of adhesive has a water absorption capacity of less than 8%.

9. The ostomy appliance wafer of claim 1, wherein the first layer of adhesive has a water absorption capacity of more than 15%.

10. The ostomy appliance wafer of claim 1, wherein the first layer of adhesive comprises moisture absorbent particles.

11. The ostomy appliance wafer of claim 1, wherein the first layer of adhesive comprises moisture absorbent particles selected from the group consisting of salts, hydrocolloids, microcolloids, and super absorbers.

12. The ostomy appliance wafer of claim 1, wherein the first layer of adhesive comprises moisture absorbent particles in a range between 5 to 30% w/w.

13. The ostomy appliance wafer of claim 1, wherein the skin facing layer of adhesive and the film layer combine to provide the ostomy appliance wafer with a measured peel force of less than 8 N force with the film layer having a moisture permeability above 1000 g/m²/24 h, and wherein the first layer of adhesive has a water absorption capacity of more than 15%.

14. An ostomy appliance wafer comprising:
   a backing layer having a distal side that defines a distal wafer surface of the ostomy appliance wafer, where the distal wafer surface is configured to receive a waste collection pouch;
   a first layer of adhesive applied to a proximal side of the backing layer;
   a film layer applied to the first layer of adhesive; and
   a skin facing layer of adhesive applied to a proximal side of the film layer and defining a proximal skin facing surface of the ostomy appliance wafer;
   wherein the skin facing layer of adhesive has a thickness in a range between 25 to 200 micrometers;
   wherein the skin facing layer of adhesive has a water absorption capacity of less than 8%.

15. An ostomy appliance wafer comprising:
   a backing layer having a distal side that defines a distal wafer surface of the ostomy appliance wafer, where the distal wafer surface is configured to receive a waste collection pouch;
   a first layer of adhesive applied to a proximal side of the backing layer;
   a film layer applied to the first layer of adhesive; and
   a skin facing layer of adhesive applied to a proximal side of the film layer and defining a proximal skin facing surface of the ostomy appliance wafer;
wherein the skin facing layer of adhesive has a thickness in a range between 25 to 200 micrometers;
   wherein the first layer of adhesive has a water absorption capacity of more than 15%.

16. An ostomy appliance wafer comprising:
   a backing layer having a distal side that defines a distal wafer surface of the ostomy appliance wafer, where the distal wafer surface is configured to receive a waste collection pouch;
   a first layer of adhesive applied to a proximal side of the backing layer;
   a film layer applied to the first layer of adhesive; and
   a skin facing layer of adhesive applied to a proximal side of the film layer and defining a proximal skin facing surface of the ostomy appliance wafer;
wherein the skin facing layer of adhesive has a thickness in a range between 25 to 200 micrometers;
   wherein the skin facing layer of adhesive and the film layer combine to provide the ostomy appliance wafer with a measured peel force of less than 8 N force with the film layer having a moisture permeability above 1000 g/m²/24 h, and wherein the first layer of adhesive has a water absorption capacity of more than 15%.

* * * * *